(12) United States Patent
Dooley

(10) Patent No.: US 9,724,223 B2
(45) Date of Patent: Aug. 8, 2017

(54) DELIVERY SYSTEM FOR A SELF EXPANDING STENT

(71) Applicant: Abbott Cardiovascular Systems Inc., Santa Clara, CA (US)

(72) Inventor: Jeffrey Dooley, Oceanside, CA (US)

(73) Assignee: ABBOT CARDIOVASCULAR SYSTEMS INC., Santa Clara, CA (US)

( * ) Notice: Subject to any disclaimer, the term of this patent is extended or adjusted under 35 U.S.C. 154(b) by 19 days.

(21) Appl. No.: 14/560,832

(22) Filed: Dec. 4, 2014

(65) Prior Publication Data

US 2016/0158049 A1    Jun. 9, 2016

(51) Int. Cl.
  *A61F 2/06*    (2013.01)
  *A61F 2/966*   (2013.01)
  *A61F 2/95*    (2013.01)

(52) U.S. Cl.
  CPC ...... *A61F 2/966* (2013.01); *A61F 2002/9517* (2013.01)

(58) Field of Classification Search
  CPC ..... A61F 2/966; A61F 2/95; A61F 2002/9517
  See application file for complete search history.

(56) References Cited

U.S. PATENT DOCUMENTS

| | | |
|---|---|---|
| 3,148,595 A | 9/1964 | Looney |
| 5,364,351 A * | 11/1994 | Heinzelman ...... A61M 25/0147 600/585 |
| 5,607,466 A | 3/1997 | Imbert et al. |
| 5,707,376 A | 1/1998 | Kavteladze et al. |
| 6,241,758 B1 | 6/2001 | Cox |
| 6,676,693 B1 | 1/2004 | Belding et al. |
| 6,945,989 B1 | 9/2005 | Betelia et al. |
| 7,052,511 B2 | 5/2006 | Weldon et al. |
| 7,758,624 B2 | 7/2010 | Dorn et al. |
| 7,854,746 B2 | 12/2010 | Dorn et al. |
| 7,985,250 B2 | 7/2011 | Kaufmann et al. |
| 8,025,692 B2 | 9/2011 | Feeser |
| 8,292,939 B2 | 10/2012 | Yachia et al. |
| 8,382,813 B2 | 2/2013 | Shumer |

(Continued)

FOREIGN PATENT DOCUMENTS

EP    2190388 B1    3/2014

OTHER PUBLICATIONS

U.S. Appl. No. 14/932,875, May 19, 2016 Non-Final Office Action.
(Continued)

*Primary Examiner* — Richard Louis
(74) *Attorney, Agent, or Firm* — Baker Botts L.L.P.

(57) ABSTRACT

A system for delivering a stent from a catheter sheath in a longitudinal direction comprising: a thumbwheel mounted on an axle, the axle being supported by opposite walls of a housing; a first pinion mounted on the axle; a second pinion mounted on the axle, whereby rotation of the thumbwheel causes rotation of the first pinion and rotation of the second pinion; a first rack, enageable with the first pinion at a first surface of the first pinion, the first rack being operably connected with a stent-engaging member; a second rack, engageable with the second pinion at a second surface of the second pinion, the second surface being disposed in a direction diametrically opposite the first surface, the second rack being operably connected with a sheath configured to confine the stent.

8 Claims, 6 Drawing Sheets

(56) References Cited

U.S. PATENT DOCUMENTS

| | | |
|---|---|---|
| 8,500,789 B2 | 8/2013 | Wuebbeling et al. |
| 8,568,467 B2 | 10/2013 | Dorn et al. |
| 8,603,045 B2 | 12/2013 | Weber |
| 8,652,193 B2 | 2/2014 | Dorn |
| 9,039,750 B2 | 5/2015 | Ryan |
| 9,078,779 B2 | 7/2015 | Dorn et al. |
| 9,095,465 B2 | 8/2015 | Kelly |
| 9,149,379 B2 | 10/2015 | Keady et al. |
| 9,192,500 B1 | 11/2015 | Longo et al. |
| 2003/0028236 A1* | 2/2003 | Gillick .................. A61F 2/95 623/1.11 |
| 2003/0191516 A1* | 10/2003 | Weldon .................. A61F 2/95 623/1.12 |
| 2005/0149159 A1 | 7/2005 | Andreas et al. |
| 2007/0156225 A1 | 7/2007 | George et al. |
| 2008/0161902 A1 | 7/2008 | Poulsen |
| 2010/0174290 A1 | 7/2010 | Wübbeling et al. |
| 2012/0053671 A1 | 3/2012 | McHugo et al. |
| 2012/0158117 A1 | 6/2012 | Ryan |
| 2012/0172963 A1 | 7/2012 | Ryan et al. |
| 2012/0221093 A1* | 8/2012 | McHugo .................. A61F 2/95 623/1.12 |
| 2014/0046428 A1* | 2/2014 | Cragg .................. A61F 2/966 623/1.12 |
| 2014/0135909 A1 | 5/2014 | Carr et al. |
| 2014/0180380 A1* | 6/2014 | Kelly .................. A61F 2/966 623/1.11 |
| 2016/0120678 A1 | 5/2016 | Green et al. |
| 2016/0120679 A1 | 5/2016 | Green et al. |
| 2016/0120680 A1 | 5/2016 | Green et al. |
| 2016/0123440 A1 | 5/2016 | Gillick et al. |
| 2016/0123441 A1 | 5/2016 | Gillick et al. |
| 2016/0123442 A1 | 5/2016 | Gillick et al. |
| 2016/0123443 A1 | 5/2016 | Gillick et al. |
| 2016/0128856 A1 | 5/2016 | Gillick et al. |

OTHER PUBLICATIONS

International Search report and Written Opinion mailed Jan. 29, 2016 in International Application No. PCT/US2015/059070.

International Search report and Written Opinion mailed Jan. 29, 2016 in International Application No. PCT/US2015/059074.

International Search report and Written Opinion mailed Jan. 29, 2016 in International Application No. PCT/US2015/059084.

* cited by examiner

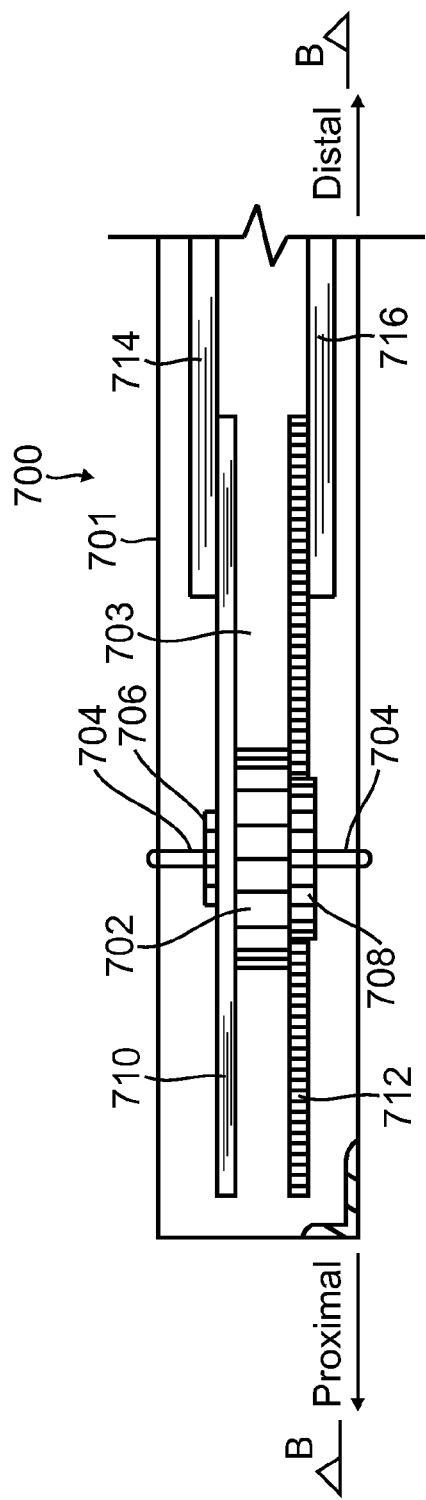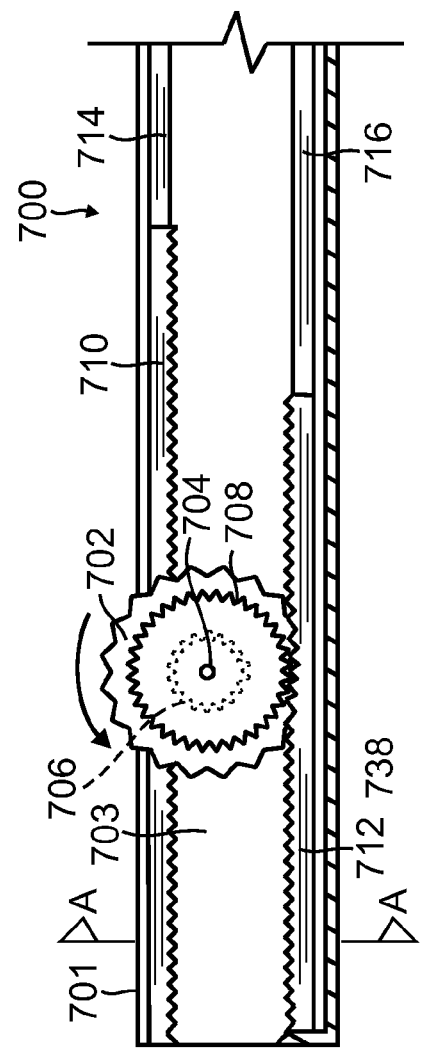
FIG. 1
FIG. 2

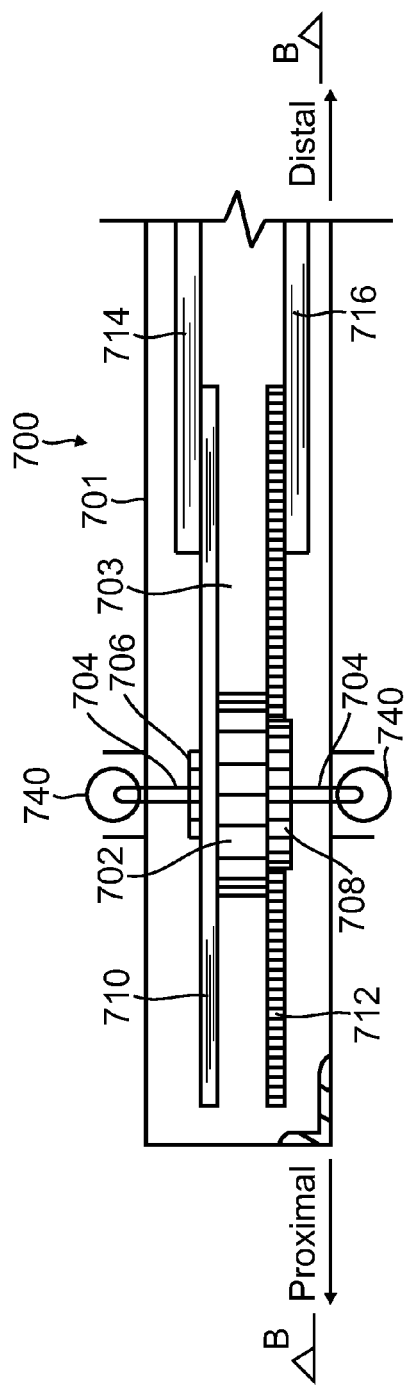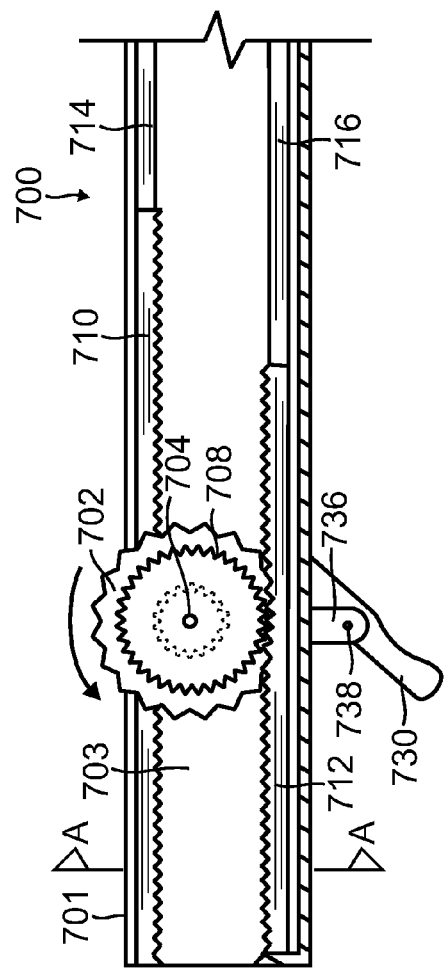

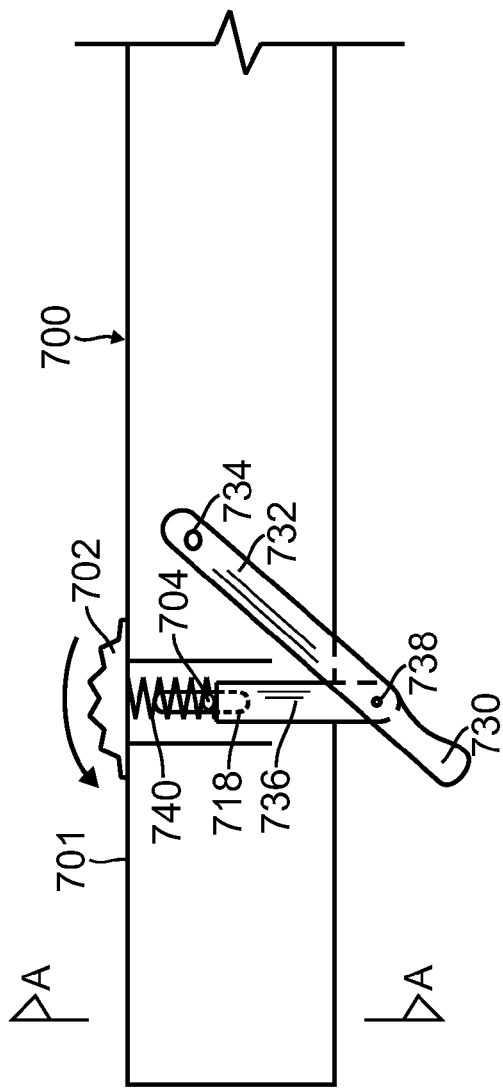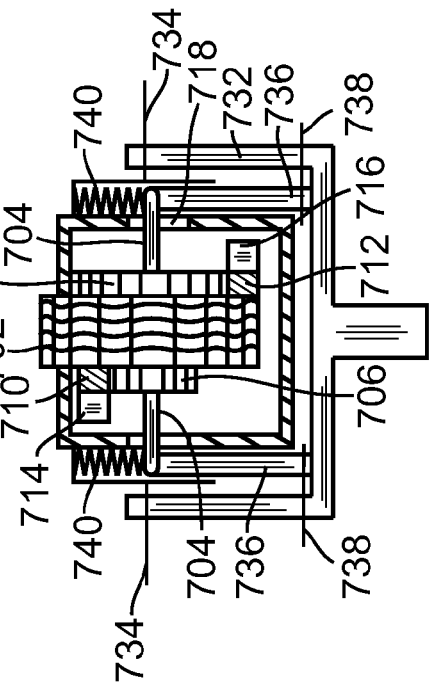
FIG. 8
FIG. 9

DELIVERY SYSTEM FOR A SELF EXPANDING STENT

CROSS-REFERENCES TO RELATED APPLICATIONS

This application is related to U.S. application Ser. No. 13/118,325, filed May 27, 2011, which is incorporated by reference herein.

BACKGROUND

This application relates to the field of delivering self-expanding stents into a body lumen of a patient. More specifically, the invention relates to providing a system for continuous stent advancement during delivery, and also for retraction of a sheath that confines the stent.

The broad concept of delivering a self-expanding stent into a body lumen of a patient is known in the art. Typically, self-expanding stent delivery involves pushing a stent so that the stent moves distally out of a confined condition within a sheath of a delivery catheter, into an expanded condition in the patient's body lumen. Typically, a delivery device is configured to push the stent distally.

However, various problems arise when this action is carried out by a delivery device that hooks (via a stent-engagement member) into the mesh of a stent before a distal force is applied to the stent-engagement member and hence to the stent.

First, a stent-engagement member that is positioned towards the rear (proximal) end of the stent may have the effect, when it is moved distally, of compressing the proximal end of the stent rather than moving the entire stent distally. This may be caused by the fact that friction against the sheath holds the distal end of the stent stationary in relation to the delivery catheter.

Second, if a stent-engagement member is positioned to engage the stent towards the front end of the stent in order to avoid the problem of compression identified above, then the stent engagement member must be made to oscillate backwards and forwards in short strokes in order to keep the stent-engagement member in contact with the mesh of the stent. (It will be appreciated that that the expansion of the stent will cause the stent-engagement member to disengage from the stent.) This oscillation requirement introduces further complexity in that the user physician must keep track of how many times he has moved the stent, and the distance of each oscillation.

Thus both methods of forcing a stent distally out of a confining sheath during deployment of a self expanding stent from a catheter are beset by problems. There is accordingly a need for a self expanding stent delivery system that address the problems in the art. The present invention addresses these and other needs.

SUMMARY OF THE INVENTION

In some embodiments, the invention is a system for delivering a stent from a catheter sheath in a longitudinal direction comprising a thumbwheel mounted on an axle, the axle being supported by opposite walls of a housing. A first pinion is mounted on the axle, and a second pinion is mounted on the axle, whereby rotation of the thumbwheel causes rotation of the first pinion and rotation of the second pinion. A first rack is provided, engageable with the first pinion at a first surface of the first pinion. The first rack is operably connected with a stent-engaging member. A second rack is provided, engageable with the second pinion at a second surface of the second pinion, the second surface being disposed in a direction diametrically opposite the first surface. The second rack is operably connected with a sheath configured to confine the stent. In further embodiments, the axle is mounted in a circular bearing in each of opposite walls of the housing, wherein the first rack and the second rack are spaced apart to allow the first pinion to be engaged with the first rack at the same time as the second pinion is engaged with the second rack. In yet further embodiments, the first pinion has a first diameter and the second pinion has a second diameter, the first diameter being different from the second diameter. In some embodiments, the axle is mounted in an elongated slot in each of opposite walls of the housing, the slot having an elongate direction that extends between the first surface and the second surface, wherein the first rack and the second rack are spaced apart to allow the first pinion to be engaged with the first rack while the second pinion is disengaged from the second rack, and separately, to allow the second pinion to be engaged with the second rack while the first pinion is disengaged from the first rack. A biasing element may be provided, and configured to bias the axle to a first end of the elongated slot, such that the second pinion is engaged with the second rack. A lever may be attached to the housing and configured to be operable by a user to urge the axle, against the biasing element, to a second end of the elongated slot opposite the first end, such that the first pinion is engaged with the first rack. Preferably, the lever is rotatably pinned to the housing.

In a different embodiment, the invention is a method of delivering a stent from a catheter sheath, the catheter being of a kind that includes a stent-engagement member, and a sheath surrounding the stent. The method comprises rolling a thumbwheel in one direction and, simultaneously with rolling the thumbwheel in one direction, both advancing the stent-engagement member and retracting the sheath. In some embodiments, advancing the stent-engagement member and retracting the sheath includes advancing the stent-engagement member by a first distance and retracting the sheath by a second distance, wherein the first distance is different from the second distance, where the first distance may be larger than the second distance.

In yet another embodiment, the invention is a method of delivering a stent from a catheter sheath, the catheter being of a kind that includes a stent-engagement member, and a sheath surrounding the stent. The method comprises engaging the stent-engagement member to be operably connected with a thumbwheel. The thumbwheel is rolled, thereby advancing the stent-engagement member. The stent-engagement member is disengaged from the thumbwheel, the sheath is engaged to be operably connected with the thumbwheel, and the thumbwheel is rolled, thereby retracting the sheath. In some embodiments, engaging the stent-engagement member includes disengaging the sheath. In some embodiments, engaging the sheath includes disengaging the stent-engaging member. In some embodiments, rolling the thumbwheel to advance the stent-engaging member, and rolling the thumbwheel to retract the sheath includes rolling the thumbwheel in the same direction in each instance of rolling the thumbwheel. In some embodiments, engaging the stent-engaging member includes operating a trigger attached to a housing of the catheter. Preferably, engaging the sheath includes operating a trigger attached to a housing of the catheter.

These and other advantages of the invention will become apparent when the specification is read in conjunction drawings and the detailed descriptions of the preferred embodiments.

BRIEF DESCRIPTION OF THE DRAWINGS

These and other features, aspects, and advantages of the present disclosure are described with reference to the drawings of certain embodiments, which are intended to illustrate certain embodiments and not to limit the invention.

FIG. 1 is a schematic top view, partially cut away, of a handle for a stent delivery catheter in which features of the invention are exemplified.

FIG. 2 is a schematic sectional side view, partially cut away, taken substantially along line B-B of FIG. 1, in which further features of the embodiment of FIG. 1 are exemplified.

FIG. 6 is a schematic top view, in partial cut away, of a handle for a stent delivery catheter showing a different embodiment of the invention.

FIG. 7 is a schematic sectional view, in partial cutaway, taken substantially along the line B-B in FIG. 6.

FIG. 8 is a schematic side view of the embodiment shown in FIG. 6.

FIG. 9 is a sectional end view, taken substantially along the line A-A in FIG. 8.

DETAILED DESCRIPTION

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Certain general aspects of stent delivery systems are described in U.S. patent application Ser. No. 13/118,325, published as U.S. Patent Pub. No. 2011/0295354, which is incorporated herein by reference in its entirety. The novel features of the invention are described in the present application.

In one embodiment, the invention is configured to provide advantageous control over both stent delivery, and sheath retraction.

Figure 3:
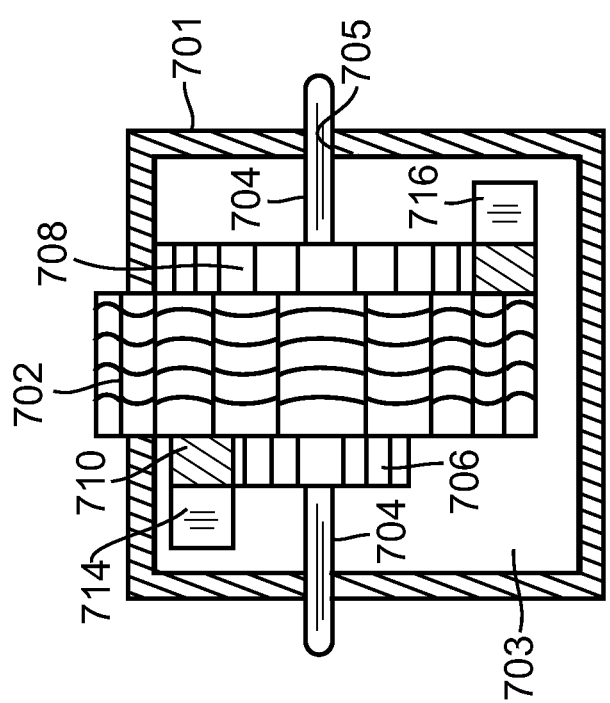
FIG. 3 is a schematic sectional end view, taken substantially along line A-A in FIG. 2.

In furtherance of enabling the stated result, reference is first made to FIGS. 1-3, where there is exemplified a handle 700 of a deployment catheter, preferably formed from two mirror image half sections of plastic or polymer to form a housing 701, joined down a center line in a known fashion. The handle has a cavity 703 into which certain actuation elements are inserted. The actuation elements of one embodiment may include a thumbwheel 702, mounted on an axle 704 so as to be rotationally fixed to the axle. The ends of the axle may be mounted in circular bearings 705 in sidewalls of the housing 701, so that the thumbwheel is suspended inside the cavity 703. On each side of the thumbwheel, and also mounted on the axle 704 within the cavity 703, are two pinions, or gears 706, 708. Both pinions are also rotationally fixed to the axle 704 so that they rotate in unison with the thumbwheel 702. As explained in more detail below, the pinions may have different diameters, to produce different mechanical advantages when the thumbwheel is rotated.

Inside the cavity 703, two racks are provided. A first rack 710 is positioned to slide axially within the cavity. To this end, upper and lower tracks (not shown in the figures) may be provided to protrude from side walls of the housing and to confine and limit the passage of the two racks to a backward and forward sliding motion. The first rack 710, having a set of teeth, is positioned to be in geared connection with the teeth of the first pinion 706, so that rotation of the thumbwheel 702 imparts a rotation to the first pinion, and hence a linear motion to the first rack 710. A second rack 712 is similarly provided to be in geared connection with the second pinion 708. Notably, however, the first rack 710 is positioned to be on the top of the first pinion 706, while the second rack 712 is positioned to be on the bottom of the second pinion 708. Thus, it will be appreciated that a single rotation of the thumbwheel 702 will cause the two racks to move in opposite directions from each other. For example, in the exemplary FIGS. 1-3, an anti-clockwise rotation of the thumbwheel will result in a backward (proximal) motion of the first rack 710, but it will also result in a forward (distal) motion of the second rack 712. It will also be appreciated that, due to the difference in diameter between the first pinion 706 and the second pinion 708, the mechanical advantage imparted to the two racks will be different, and the speed of their motions (besides being in opposite directions) will be different under a uniform motion of the thumbwheel. This aspect of the configuration of the embodiment may be utilized to advantageous effect as will be more fully explained below.

Attached to each rack is a tie. Thus, a first tie 714 is attached to the first rack 710. A second tie 716 is attached to the second rack 712. Thus, linear movement of each rack imparts an equivalent movement to each associated tie. Each tie, in turn extends through a central portion of the catheter according to known principles. The central portion of the catheter is not shown in the figures, but will be readily envisaged by those of ordinary skill.

Figure 4:
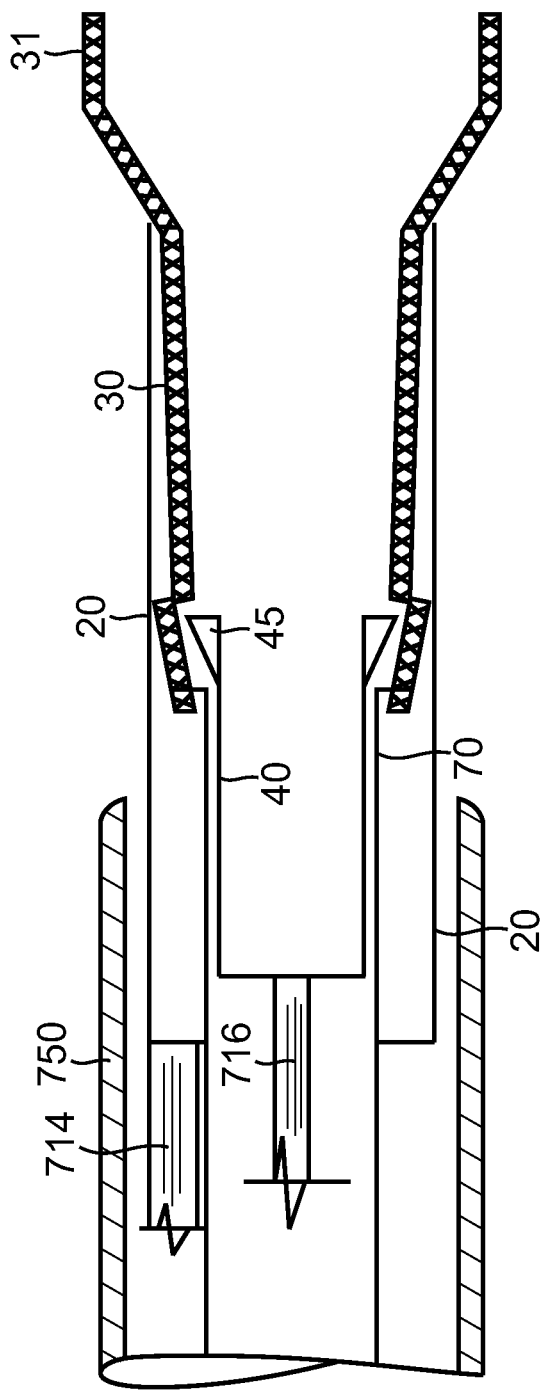
FIG. 4 is a schematic sectional view of a distal end of the stent delivery catheter of which the handle is shown in FIG. 1, and in which further features of the invention are exemplified.

Turning to FIG. 4, this figure shows, schematically in section, the distal end portion of the stent delivering catheter. It shows the relationship between a stent engaging member 45, a sheath 20, and the two ties 714 and 716 which have been previously described in the context of the handle. As noted, the ties extend as linear elements all the way from the handle 700 of the catheter to the distal end portion shown in FIG. 4. As seen in FIG. 4, a self expanding stent 30 is confined within the sheath 20. A stent engaging member 45 (which may comprise a pair of opposite stent engaging members 45) is positioned within the internal lumen of the stent 30. The stent engaging members comprise sharp forwardly pointing hooks, and are mounted on spring loaded arms or biasing elements 40 that are shaped to urge the stent engaging members radially outwardly, so as to engage with the fabric of the self expanding stent. Distal movement of the stent engaging members 45 will cause the stent engaging members to lodge in the fabric of the stent, and move the stent distally, as may be envisaged with reference to FIG. 4, which shows the sharp points of the stent engaging member 45 partially distorting the proximal fabric of the stent. As the stent is forced distally to emerge from the sheath 30, the distal tip 31 of the stent expands radially outwardly, as seen in FIG. 4. The stent-engaging member 45 of FIG. 4 may be similar to that exemplified and described with reference to FIG. 8, of application Ser. No. 13/118,325 (incorporated by reference).

Also shown in FIG. 4 is a chord 70 that may be used to pull the stent back into the sheath in the event of a mishap, and the surgeon elects to abort the procedure. The chord 70 is known in the art and is not further described herein.

In the present invention, the second tie 716 is operably connected to a stent-engaging member 45 via a biasing element 40. It will be appreciated that linear movement of the second rack 712 via the thumbwheel will be followed by a corresponding and equal linear movement of the stent-engaging member 45.

The first tie 714 is operably connected to the sheath 20 which surrounds the stent 30. The connection between first tie 714 and sheath 20 is exemplified in FIG. 4. It will be appreciated that linear movement of the first rack 710 via the thumbwheel will be followed by a corresponding and equal linear movement of the sheath 20.

In further description of FIG. 4, an outside guide catheter 750 may be provided to enclose the stent and its delivery mechanism during delivery of the catheter to the desired location in the vasculature of the patient.

Figure 5A:
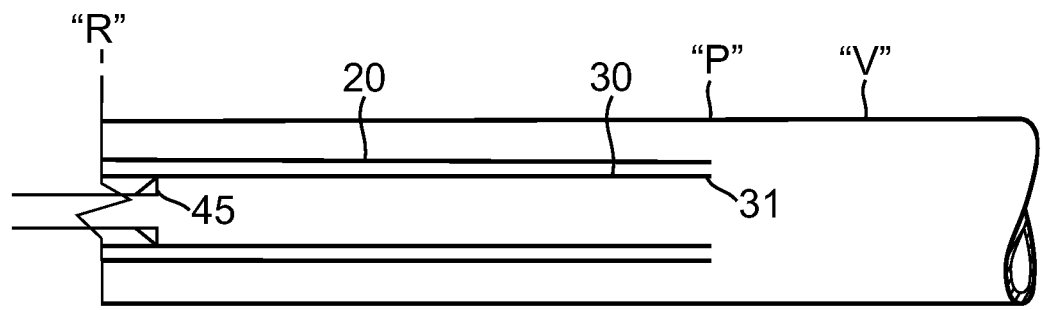
FIGS. 5A-5C show schematic views of a stent emerging from a sheath inside a body lumen, following features of the invention.
Figure 5B:
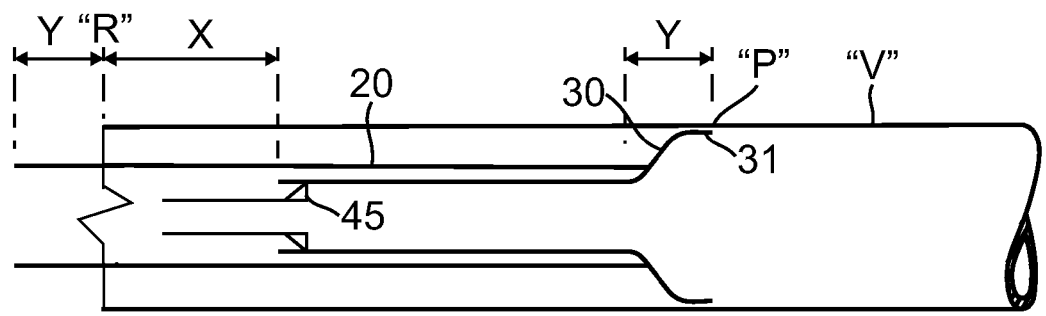
Figure 5C:
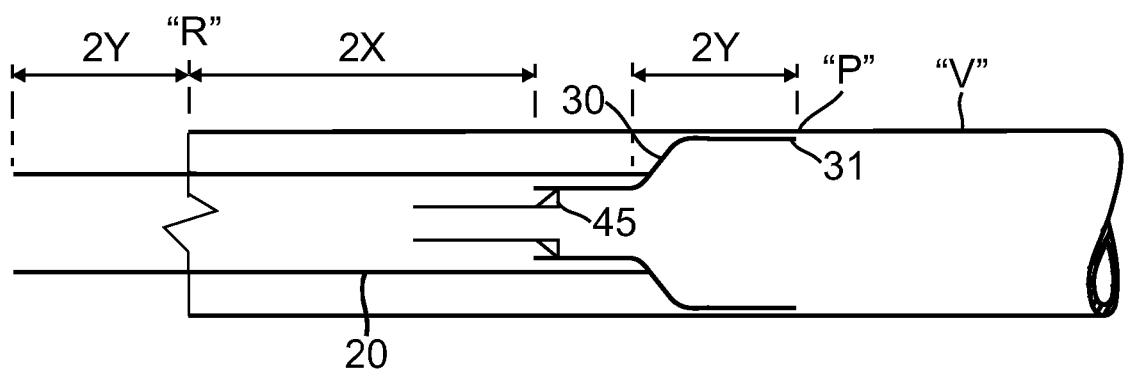

It will be appreciated with reference to FIG. 4 in combination with FIGS. 5A-5C that a distal movement of, let us say, X units of length by the stent-engaging element 45 will advance the stent in its collapsed configuration by X units of distance. However, when that length of stent emerges from the sheath 20, the expanding stent will shorten in length so that the net increment in the length of the expanded portion of the stent is less than X units, say Y units. Thus, if the physician wishes for the stent that has emerged from the sheath to (a) remain anchored by its distal tip 31 in a fixed position within the vessel of the patient and, (b) at the same time, the physician wants to keep the proximal end of the catheter stationary, then he will need to ensure that the sheath is retracted by a distance equal to Y units.

This feature is demonstrated schematically in FIG. 5A-5C. FIG. 5A shows the stent 30 and the sheath 20 are initially aligned at their distal tips before any advancement of the stent or retraction of the sheath. A reference point "R" is shown in the figures to indicate a schematic reference point in relation to the vessel wall "V" where the stent and sheath are in initial alignment with each other. Then, moving to FIG. 5B, there is exemplified how if the stent 30 is advanced at the proximal end by a stent-engagement member 45 by a distance of X units, then the sheath must be withdrawn by Y units if the catheter as a whole is to be maintained motionless in relation to the body of the patient while, at the same time, maintaining the contact point of the stent tip 31 against the vessel wall "V" at a motionless point "P". Significantly, because the stent expands as it emerges from the sheath, the distance Y must be less than the distance X. Then, moving to FIG. 5C, there is exemplified how if the stent 30 is advanced at the proximal end by a stent-engagement member 45 by a distance of 2X units, then the sheath must be withdrawn by 2Y units if the catheter as a whole is to be maintained motionless in relation to the body of the patient while, at the same time, maintaining the contact point of the stent tip 31 against the vessel wall "V" at the motionless point "P".

In one embodiment, the invention introduces a solution to automatically satisfy the geometric requirement described above. The solution is to provide first and second pinions that have differently sized diameters so that the ratio of the diameter of the first pinion 706 to the diameter of the second pinion 708 is Y:X.

It will be appreciated by those of ordinary skill that under these conditions, rolling the thumb wheel backward (anti-clockwise) as indicated in FIG. 2 will result in the first rack 710 retracting a first distance, and the second rack 712 advancing a second distance, such that the ratio of the first distance to the second distance is Y:X. By corollary, under the structure described, the sheath 20 will retract by the first distance, and the stent engagement member 45 will advance by the second distance, in the same ratio. Thus, it will be apparent that if the surgeon holds the catheter in a stationary position in relation to the body of the patient, and rolls the thumbwheel 702 anti-clockwise, then the stent 30 will advance and the sheath 20 will retract by amounts respectively that conveniently allow the surgeon to hold the catheter stationary, while the stent emerges from the sheath without dislodging the connection between the distal tip 31 of the stent and the vessel wall "V" as seen in FIGS. 5A-5C.

The foregoing is an advantageous result, because the physician user may confidently move the thumbwheel and hold the catheter stationary in relation to the patient's body, knowing that the tip of the stent will remain in stationary contact with the vessel wall, and will not slide against the vessel wall with potentially catastrophic effects in the form of dislodging plaque from the wall.

In another embodiment, features of the previous embodiment may be utilized, along with additional or modified structure that will now be described. Elements of FIG. 6-FIG. 9 exemplify these additional or modified structural features, and they may be utilized to give the physician a different type of control over the advancement of the stent and retraction of the sheath than that described above. In this embodiment, the axle 704 may be mounted within an elongate slot 718 (seen in FIGS. 8, 9), which extends vertically, in opposite walls of the housing 701. Thus, the assembly that includes the axle with the thumbwheel and two pinions mounted on the axle can be elevated or depressed by a small distance in relation to the housing. In this embodiment, the first rack 710 and the second rack 712 are spaced slightly further apart from each other in a vertical direction than in the previous embodiment, so that only one pinion can be placed in contact with one rack at any given moment. In order to allow the physician to elect which rack should be engaged via the thumbwheel, a trigger 730 is provided. The trigger comprises a "Y" shaped structure with arms 732 that flank the housing 701. The arms are fixed with pins 734 to the housing (FIGS. 8 and 9), allowing the trigger to rotate beneath the housing. On each side of the housing, a vertically extending rod 736 is provided. At a lower end, each rod is fixed with a pin 738 to the trigger. At an upper end of each rod, the rod abuts the axle 704. Above each end of the axle a biasing element 740, preferably a spring, is located to bias the axle in a downward direction. Under this configuration, the physician user may pull the trigger 730 proximally with his forefinger. This action will elevate each rod 736, and thus elevate the ends of the axle against the bias of the biasing elements 740. Elevating the axle will urge the first pinion 706 into contact with the first rack 710, but will disengage the second pinion 708 from the second rack 712. Conversely, if the physician user releases his pull on the trigger, the biasing elements 740 will bias the axle downward in the absence of any force opposing such bias. Downward movement of the axle 704 results in engagement of the second pinion 708 with the second rack 712, but disengagement of the first pinion 706 from the first rack 710.

Thus, it will be appreciated that this modified structure gives the physician user a choice in which he may select to engage the thumb wheel 702 with either the stent-engaging member 45 for advancement of the stent, or alternatively the sheath 20 for retraction of the sheath. It will be understood that by providing an election to the physician user results in a delivery mechanism that operates under a different principle than the foregoing embodiment. Here, the physician may wish to follow more closely the actual rate of delivery of the stent through the sheath using conventional means such as radiopaque markers, and if his observation causes him to conclude, for example, that the stent is in fact becoming compressed within the sheath rather than emerging from the end of the sheath, he may decide to pull the sheath back a little faster. Additionally, the structure of this embodiment allows the user to repeatedly advance the stent without retracting the sheath, but to subsequently retract the sheath without advancing the stent. The present invention gives the user this option, which may be required by the user under conditions in which the geometry of the vasculature requires a repeated advancement of the stent rather than a single forward movement of the stent.

Thus there is described a delivery system that provides advantages over prior art delivery systems, and addresses needs in the art.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

I claim:

1. A system for delivering a stent from a catheter sheath in a longitudinal direction comprising:
   a thumbwheel mounted on an axle, the axle being supported by opposite walls of a housing;
   a first pinion mounted on the axle;
   a second pinion mounted on the axle, whereby rotation of the thumbwheel causes rotation of the first pinion and rotation of the second pinion;
   a first rack, enageable with the first pinion at a first surface of the first pinion, the first rack being operably connected with a stent-engaging member;
   a second rack, engageable with the second pinion at a second surface of the second pinion, the second surface being disposed in a direction diametrically opposite the first surface, the second rack being operably connected with a sheath configured to confine the stent;
   wherein the axle is mounted in an elongated slot in each of the opposite walls of the housing, each slot having an elongate direction that extends between the first surface and the second surface, and wherein the first rack and the second rack are spaced to allow the first pinion to be engaged with the first rack while the second pinion is disengaged from the second rack, and separately, to allow the second pinion to be engaged with the second rack while the first pinion is disengaged from the first rack;
   a biasing element configured to bias the axle to a first end of the elongated slot of each sidewall, such that the second pinion is engaged with the second rack;
   a trigger coupled to the axel by rods and configured to be operable by a user to urge the axle, against the bias of the biasing element, to a second end of the elongated slot of each sidewall opposite the first end, such that the first pinion is engaged with the first rack.

2. The system of claim 1, wherein the trigger is rotatably pinned to the housing.

3. A method of delivering a stent from a catheter sheath, the catheter being of a kind that includes a stent-engagement member, and a sheath surrounding the stent, the method comprising:
   engaging the stent-engagement member to be operably connected with a thumbwheel via at least a first rack;
   rolling the thumbwheel, thereby advancing the stent-engagement member;
   disengaging the stent-engagement member from the thumbwheel;
   engaging the sheath to be operably connected with the thumbwheel via at least a second rack; and
   rolling the thumbwheel, thereby retracting the sheath,
   wherein a biasing element is configured to bias an axel of the thumbwheel toward the second rack, such that the thumbwheel is operably connected to the second rack via the axel, and
   a trigger is coupled by rods to the axel and operable by a user to urge the axel against the bias of the biasing element toward the first rack to operably connect the thumbwheel to the second rack.

4. The method of claim 3, wherein engaging the stent-engagement member includes disengaging the sheath.

5. The method of claim 3, wherein engaging the sheath includes disengaging the stent-engaging member.

6. The method of claim 3, wherein rolling the thumbwheel to advance the stent-engaging member, and rolling the thumbwheel to retract the sheath includes rolling the thumbwheel in the same direction in each instance of rolling the thumbwheel.

7. The method of claim 3, wherein engaging the stent-engaging member includes operating the trigger attached to a housing of the catheter.

8. The method of claim 3, wherein engaging the sheath includes operating the trigger attached to a housing of the catheter.

* * * * *